United States Patent [19]

Evans et al.

[11] Patent Number: 6,083,882
[45] Date of Patent: Jul. 4, 2000

[54] ACYLCYCLOHEXANEDIONE PLANT GROWTH REGULATOR FOR CONTROL OF OVERALL NUTRITIVE VALUE OF ALFALFA

[75] Inventors: John R. Evans, Raleigh, N.C.; Richard R. Evans, Greenville, Miss.

[73] Assignee: BASF Corporation, Mt. Olive, N.J.

[21] Appl. No.: 09/321,398

[22] Filed: May 28, 1999

Related U.S. Application Data

[60] Provisional application No. 60/087,391, May 30, 1998.
[51] Int. Cl.[7] ................................................ A01N 37/08
[52] U.S. Cl. ............................. 504/313; 504/320; 504/348
[58] Field of Search ..................................... 504/313, 348, 504/320

[56] References Cited

U.S. PATENT DOCUMENTS

| | | | |
|---|---|---|---|
| 4,560,403 | 12/1985 | Motojima et al. | 71/106 |
| 4,693,745 | 9/1987 | Brunner | 71/94 |
| 5,869,424 | 2/1999 | Rademacher et al. | 504/130 |

OTHER PUBLICATIONS

*Can. J. Plant Sci.* 68:95–101, Jan. 1988.

*Primary Examiner*—S. Mark Clardy

[57] ABSTRACT

Applying an effective amount of an acylcyclohexanedione plant growth regulator to a growing pre-harvest alfalfa plant improves the overall stature and overall nutritive value of alfalfa at harvest.

2 Claims, No Drawings

ACYLCYCLOHEXANEDIONE PLANT GROWTH REGULATOR FOR CONTROL OF OVERALL NUTRITIVE VALUE OF ALFALFA

This application claims the benefit of copending U.S. Provisional Application No. 60/087,391, filed May 30, 1998.

FIELD OF THE INVENTION

The invention relates to a method of controlling the fiber, digestible nutrients and crude protein in alfalfa. Specifically, it relates to the application of a acylcyclohexanedione Plant Growth Regulator to alfalfa sufficient to improve overall alfalfa quality.

BACKGROUND OF THE INVENTION

Alfalfa (*Medicago sativa*) is a forage crop grown primarily for its nutritive properties. Crude protein is the measure of the total nitrogen in a forage. It includes true plant proteins and non-protein nitrogen compounds, both of which are useable by ruminant animals. High protein content is the primary reason that legumes such as alfalfa are grown for forage. Another important measure of nutritive value for forage crops is how digestible the crop is. Acid detergent fiber (ADF) is that portion of the forage remaining after treatment with detergent under acidic conditions. ADF measures cellulose, lignin, and silica. As the value of ADF increases, the forage becomes less digestible. Lastly, nutritive value of the forage measured by percent total digestible nutrients (TDN) which is equal to the sum of percent digestible protein, percent digestible crude fiber, percent digestible starch and sugar and percent digestible fat.

Plant growth regulators (PGR's) are used in a wide variety of crops. There are a number of different types of PGR's, including anti-gibberellin, auxin-like, anti-auxins, and ethylenegenerators which have a wide ranging and unpredictable effect.

Prohexadione belongs to a new family of plant growth regulators (acylcyclohexanedione type plant growth regulators). These growth regulators block the biosynthesis of gibberellin (GA). Gibberellin is mainly responsible for controlling cell elongation. When gibberellin biosynthesis is blocked, plant cells will divide normally but the cells will be shorter. This results in shorter plants (reduced stature). Inhibitors of gibberillin biosynthesis are used in many crops to reduce stature, prevent lodging and the like. U.S. Pat. No. 4,560,403 describes prohexadione (3-hydroxy4-propionyl-5-oxo-3-cyclohexene carboxylic acid) and a number of other compounds of a class of cyclohexene plant growth regulators.

No information to date has been available on the actual effect of this new group of growth retardants, the acylcyclohexanediones, on alfalfa.

Plant growth regulators have been tested for further effects on the nutritive value and yield of alfalfa (*Can. J. Plant Sci.* 68:95–101). PGR's were tested from various classes of PGR's including anti-gibberellins; however, no acylcyclohexanedione types were tested. The results varied with all groups and appear to be total unpredictable, with both positive and negative neutral results both overall and for individual parameters. Within the anti-gibberellin group, both positive and negative effect were shown on ADF. In some cases, the results showed a complete reversal of effects in successive years. However, to date, none of the anti-gibberellin PGR's have shown a positive effect on total protein. So, while they have improved certain aspects of the nutritive value of alfalfa, none have improved all the parameters which comprise the nutritive value of alfalfa.

It appears that due to the lack of consistent results, both positive and negative, with plant growth regulators; the large number of compounds disclosed in the prior art; the lack of any test data in the art which would show the effects of prohexadione; the unpredictability of anti-gibberellin compounds on the art; the lack of any effect in total protein in the art that any reference is merely an invitation to experiment with these compounds in alfalfa.

It would be highly desirable that a PGR decrease ADF, increase TDN and increase Total Protein in alfalfa to improve the overall nutrient value of the alfalfa. It would be useful, in general, to accomplish this without significant crop injury that can occur with PGR applications; and to have the possibility of normal stature of the plant at some point after treatment.

SUMMARY OF THE INVENTION

It has been surprisingly found that acylcyclohexanedione type PGR's, preferably cyclohexene PGR's, most preferably those that block the biosynthesis of gibberellin, can be used to improve the nutritive quality of alfalfa in three areas, namely ADF, TDN and Total Protein. They solve the above problems as well as others that will become clear from the disclosure.

Accordingly, provided herein is a method for improving the overall nutritive value of alfalfa comprising applying an effective amount of an acylcyclohexanedione plant growth regulator to a growing pre-harvest alfalfa plant sufficient to improve the overall nutritive value of alfalfa at harvest.

DETAILED DESCRIPTION OF THE INVENTION

Compounds that may be used to practice particular embodiments of the invention include those described in U.S. Pat. No. 4,560,403, incorporated herein by reference, as represented by the formula:

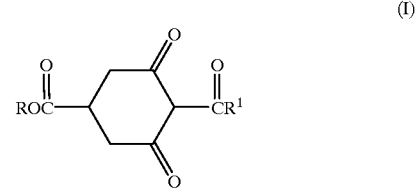

(I)

wherein R represents a hydrogen atom or an alkyl group, an alkylthioalkyl group or an unsubstituted or substituted phenyl group; and $R^1$ represents an alkyl group, an unsubstituted or substituted benzyl group, a phenethyl group, a phenoxymethyl group, a 2-thienylmethyl group, an alkoxymethyl group or an alkylthiomethyl group, or a salt of said cyclohexane compound.

A preferred compound for use in practicing embodiments of the present invention is prohexadione represented by the formula:

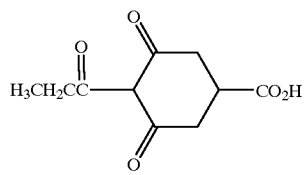

(II)

As used herein, prohexadione includes the compound (IUPAC name) 3,5-dioxo4-propionylcyclohexanecarboxylic acid (or 3,5-dioxo4-(1-oxopropyl)cyclohexanecarboxylic acid (C.A. name)) and also 3-hydroxy4-prionyl-5-oxo-3-cyclohexene carboxylic acid and its pharmacological effective salts for example a chloride, sulfate, metrab, acetate, carbonate, hydride, hydroxide, sodium, potassium, calcium, magnesium, barium, aluminum, nickel, copper, manganese, cobalt zinc, iron or silver. The preferred compound for use in preferred embodiments of the invention is prohexadione calcium and is represented by the formula:

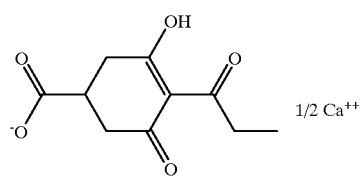

(III)

In another aspect of the invention, the method may also be practiced with compounds described in U.S. Pat. No. 4,693,745, incorporated herein by reference, represented by the formula:

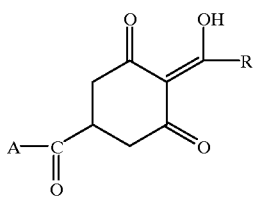

(IV)

wherein

A is an —$OR_2$ or —$NR_3R_4$ radical,

R is $C_3$–$C_6$ cycloalkyl, $R_2$ $R_3$ and $R_4$ are each independently hydrogen, $C_1$–$C_6$alkyl, $C_1$–$C_6$haloalkyl, $C_2$–$C_{10}$alkoxyalkyl, $C_2$–$C_{10}$alkylthioalkyl, $C_3$–$C_6$alkenyl, which is unsubstituted or substituted by halogen, $C_1$–$C_4$alkoxy or $C_1$–$C_4$alkylthio; $C_3$–$C_6$alkynyl; phenyl or $C_1$–$C_6$aralkyl, wherein the phenyl nucleus is unsubstituted or substituted by halogen, $C_1$–$C_4$alkyl, $C_1$–$C_4$alkoxy, $C_1$–$C_4$haloalkyl, nitro or cyano; one of $R_3$ and $R_4$ is methoxy; or $R_3$ and $R_4$, together with the nitrogen atom to which they are attached, form a 5-or 6-membered heterocyclic ring system which may contain an additional oxygen or sulfur atom in the ring; and the metal or ammonium salts thereof.

Specific compounds of the immediately above noted formula, for use in practicing embodiments of the invention include trinexapac (IUPAC name 4-cyclopropyl(hydroxy)methylene-3,5-dioxyocyclohexanecarboxylic acid) and preferably its ethyl ester, trinexapac-ethyl (IUPAC name, ethyl 4-cyclopropyl(hydroxy)methylene-3,5-dioxocyclohexanecarboxylate; CA name, ethyl 4-(cyclopropylhydroxymethylene)-3,5-dioxyocyclohexanecarbocylate) represented by the formula:

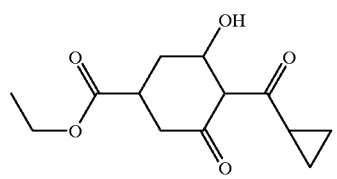

(V)

By overall nutritive value of alfalfa is meant a combination of a decrease in the ADF, an increase in the TDN and an increase in the Total Crude Protein. It may also include the ability to rebound or continue with increased growth after treatments and do this without significant injury to the alfalfa crop.

Preferably the appropriate compounds of the present invention are applied while the plant is still growing. The compound should be applied before the plant is cut for harvest in order to obtain the maximum benefit of the invention.

The compounds of this invention may be used directly in alfalfa, but are more conveniently formulated into compositions for such usage.

The compounds and salts can be applied in a number of ways, for example, they can be applied, formulated or unformulated, directly to the foliage of alfalfa or they can be sprayed on, dusted on or applied as a cream or paste formulation or they can be applied as slow release granules.

The compositions may be in the form of dusting powders or granules comprising the active ingredient and a solid diluent or carrier, for example fillers such as kaolin, bentonite, dolomite, calcium carbonate, talc, powdered magnesia, Fuller's earth, gypsum, diatomaceous earth and China clay.

The compositions may also be in the form of dispersible powders, granules or grains comprising a wetting agent to facilitate the dispersion in liquids of the powder or grains which may contain also fillers and suspending agents.

The aqueous dispersions or emulsions may be prepared by dissolving the active ingredient in an organic solvent optionally containing wetting, dispersing or emulsifying agent(s) and then adding the mixture to water which may also contain wetting, dispersing or emulsifying agents(s). Suitable organic solvents are kerosene, cyclohexanone, methylethyl ketone, acetone, methanol, acetonitrile, and the like.

The compositions may also be in the form of liquid preparations for use as dips or sprays which are generally aqueous dispersions or emulsions containing the active ingredient in the presence of one or more of wetting agent(s), dispersing agent(s), emulsifying agent(s) or suspending agent(s). The agents can be anionic or nonionic agents.

The compositions for use as aqueous dispersions or emulsions are generally supplied in the form of a concentrate containing a high proportion of the active ingredient.

The composition of this invention may usually be formulated into a wettable powder comprising 5 to 95%, preferably 10 to 50% by weight of the new compounds of this invention as active ingredient; 1 to 20%, preferably 5 to 10% by weight of surfactant; and 4 to 44%, preferably 40 to 85% by weight of solid carrier, the solid carrier being preferably ammonium sulfate.

The composition of this invention may be formulated into an emulsifiable concentrate (EC) comprising 5 to 95%, preferably 20 to 70% by weight of the new compound of this invention as active ingredient; 1 to 40%, preferably 5 to 20% by weight of surfactant; and 4 to 94%, preferably 10 to 75% by weight of liquid carrier.

The composition of this invention may be made up as granules comprising 0.5 to 40%, preferably 2 to 10% by weight of the new compound of this invention as active ingredient; 1 to 20%, preferably 2 to 10% by weight of the surfactant; and 40 to 98.5%, preferably 20 to 96% by weight of solid carrier. And, the composition of this invention may be formulated into dust comprising 0.5 to 10%, preferably 1 to 5% by weight of the active ingredient; and 99.5 to 90%, preferably 99 to 95% by weight of finely divided solid carrier.

The composition of this invention may also be formulated into a paste comprising 0.1 to 20%, preferably 1 to 10% by weight of the active ingredient, 1 to 20%, preferably 2 to 10% by weight of surfactant; and 60 to 98.9%, preferably 80 to 97% by weight of paste base.

The rate of application will vary based on the particular plant size and spacing at the time of application. More exact amounts can be determined at the time of use by one skilled in the art. The rate of application of the compound of this invention may be in the range of 5 g to 1000 g per hectare and preferably 25 g to 300 g per hectare as the active ingredient.

The applications are preferably made when the plants are from 10 cm to 40 cm upright growth.

The following examples are representative of the invention only and are not intended to be limiting; one skilled in the art will be able to fully practice the invention based on the disclosure and claims, and the examples.

EXAMPLE 1

A formulation containing 10% prohexadione calcium with 60% ammonium sulfate (used as a carrier) and other inert ingredients was prepared. Experiments were conducted in a similar manner at several different sites across the United States. Applications of the formulation were made with hand held sprayer booms delivering between 10 and 40 gallons of spray volume per acre. The rates of application of the formulation are expressed in terms of active ingredient per hectare and were performed at 0, 0.0347, 0.0701 and 0.140 kg active ingredient (ai) per hectare (kg ai/ha). These rates were applied at two timings, A and B. Timing A was when the alfalfa was at about 12 to 18 cm of upright growth. Timing B was one week following A.

After treatment the alfalfa was harvested at three different dates called harvest X, Y, and Z. Harvest X was made when the alfalfa was at the growth stage called first flower. Harvest Y and Z were collected at 4–5 days and 8–10 days respectively after harvest X.

The alfalfa samples were harvested and analyzed.

Relative Feed Value (RFV) was measured and the results are displayed in Table 1. RFV is an index used to rank cool season perennial forage crops by their potential intake of digestible dry matter. RFV is obtained by multiplying the digestible dry matter times the dry matter intake and dividing by 1.29.

TABLE 1

RELATIVE FEED VALUE INDEX OF PROHEXADIONE TREATED ALFALFA

| | Prohexadione | | Harvest | | |
|---|---|---|---|---|---|
| tmt #s | Ca kg ai/ha | Application | X | Y | Z |
| | | | Relative Feed Value Index | | |
| 1.8.15 | 0 | | 172.8 | 161.1 | 156.2 |
| 2.9.16 | 0.0347 | A | 175.6 | 166.4 | 163.2 |
| 3.10.17 | 0.0701 | A | 177.9 | 166.2 | 160.1 |
| 4.11.18 | 0.140 | A | 184.2 | 173.7 | 163.4 |
| 5.12.19 | 0.0347 | B | 172.1 | 166.8 | 166.0 |
| 6.13.20 | 0.0701 | B | 179.1 | 173.7 | 159.3 |
| 7.14.21 | 0.140 | B | 184.4 | 176.1 | 171.2 |

N = 8 locations
Application A = 5–7 inches of upright growth
Application B = one week later
Harvest X = first flower
Harvest Y = 4–5 days after X
Harvest Z = 8–19 days after X RFV is known to decrease as harvest is delayed. As expected, the RFV of the untreated plots decreased as harvest was delayed. Prohexadione calcium applied at timing A increased the RFV by 3 to 12 points. A dramatic increase in RFV occurred with the highest rate of prohexadione calcium. The RFV increase with prohexadione calcium was noted at each of the three harvest dates (X, Y and Z), but the most consistent increases occurred at the earlier harvest dates (X and Y).

Application of prohexadione calcium at timing B also resulted in increased RFV, especially at the 0.140 kg ai/ha rate. The increases in RFV at the lower rates were not as consistent at timing B as compared to timing A. However, individual treatments at timing B at the lower rates still proved dramatic increases of over 9 points.

Crude protein was measured and the results are displayed in Table 2. Crude protein is a measure of the total nitrogen in the forage. It includes true plant proteins and non-protein nitrogen compounds, both of which are usable by ruminant animals.

TABLE 2

PERCENT CRUDE PROTEIN OF PROHEXADIONE TREATED ALFALFA

| | Prohexadione | | Harvest | | |
|---|---|---|---|---|---|
| tmt #s | Ca kg ai/ha | Application | X | Y | Z |
| | | | Percent Crude Protein | | |
| 1.8.15 | 0 | | 22.2 | 20.4 | 19.3 |
| 2.9.16 | 0.0347 | A | 22.1 | 21.1 | 20.5 |
| 3.10.17 | 0.0701 | A | 22.9 | 21.0 | 20.3 |
| 4.11.18 | 0.140 | A | 23.4 | 21.6 | 20.8 |
| 5.12.19 | 0.0347 | B | 22.3 | 21.1 | 21.1 |
| 6.13.20 | 0.0701 | B | 22.8 | 21.5 | 20.4 |
| 7.14.21 | 0.140 | B | 23.2 | 21.4 | 21.1 |

N = 8 locations
Application A = 5–7 inches of upright growth
Application B = one week later
Harvest X = first flower
Harvest Y = 4–5 days after X
Harvest Z = 8–19 days after X Percent crude protein was increased by the prohexadione calcium treatments applied at rates of 0.0701 and 0.140 kg ai/ha. This increase was observed at both application dates (A and B). Even the lowest prohexadione calcium tended to increase crude protein in the alfalfa forage.

Percent total digestible nutrients (TDN) was measured and the results are displayed in Table 3. TDN is equal to the sum of percent digestible crude protein, percent digestible crude fiber, percent digestible starch and sugars, and percent digestible fats time 2.25. The fats are multiplied by 2.25 because they contain that much more energy per unit weight.

TABLE 3

TOTAL DIGESTIBLE NUTRIENTS OF PROHEXADIONE TREATED ALFALFA

| | Prohexadione | | Harvest | | |
|---|---|---|---|---|---|
| tmt #s | Ca kg ai/ha | Application | X | Y | Z |
| | | | Total Digestible Nutrients | | |
| 1.8.15 | 0 | | 40.5 | 39.9 | 39.1 |
| 2.9.16 | 0.0347 | A | 40.9 | 40.4 | 39.8 |
| 3.10.17 | 0.0701 | A | 41.1 | 40.2 | 39.3 |
| 4.11.18 | 0.140 | A | 41.9 | 40.9 | 39.4 |
| 5.12.19 | 0.0347 | B | 40.9 | 40.0 | 41.3 |
| 6.13.20 | 0.0701 | B | 40.9 | 40.5 | 38.9 |
| 7.14.21 | 0.140 | B | 41.8 | 41.3 | 40.1 |

N = 8 locations
Application A = 5–7 inches of upright growth
Application B = one week later
Harvest X = first flower
Harvest Y = 4–5 days after X
Harvest Z = 8–19 days after X The data of Table 3 shows that the TDN of the untreated plots decreased as harvest was delayed. This is the same trend as noted with Relative Feed Value, i.e. that alfalfa quality decreases as harvest is delayed . Prohexadione calcium applied at timing A increased the RFV by as much as 1.8 points. The most dramatic increase in TDN occurred with the highest rate of prohexadione calcium (0.140 kg ai/ha). The RFV increase with prohexadione calcium was noted at each of the three harvest dates (X, Y and Z)

Application of prohexadione calcium at timing B also resulted in increased TDN. Indeed, the most dramatic increase in TDN (1.9 points) occurred with the highest rate of prohexadione calcium at timing B.

The invention has been described with reference to various specific embodiments. However, many variations and modifications may be made while remaining within the scope and spirit of the invention.

What is claimed is:

1. A method of improving the overall nutritive value of alfalfa comprising: applying an effective amount of an acylcyclohexanedione plant growth regulator to a growing pre-harvest alfalfa plant sufficient to improve the overall stature, overall nutritive value of alfalfa at harvest.

2. A method according to claim 1 wherein the PGR is prohexadione.

* * * * *